(12) United States Patent
Feistel et al.

(10) Patent No.: US 9,173,912 B2
(45) Date of Patent: Nov. 3, 2015

(54) CISTUS EXTRACT CONTAINING ENRICHED SECONDARY PLANT INGREDIENTS

(75) Inventors: Bjoern Feistel, Andernach (DE); Bernd Walbroel, Koenigswinter (DE)

(73) Assignee: Finzelberg GmbH & Co. KG, Andemach (DE)

( * ) Notice: Subject to any disclaimer, the term of this patent is extended or adjusted under 35 U.S.C. 154(b) by 126 days.

(21) Appl. No.: 12/990,878

(22) PCT Filed: May 6, 2009

(86) PCT No.: PCT/EP2009/055487
§ 371 (c)(1),
(2), (4) Date: Nov. 18, 2010

(87) PCT Pub. No.: WO2009/135880
PCT Pub. Date: Nov. 12, 2009

(65) Prior Publication Data
US 2011/0059190 A1    Mar. 10, 2011

(30) Foreign Application Priority Data

May 6, 2008 (EP) ..................................... 08155699

(51) Int. Cl.
*A61K 36/752* (2006.01)
*A61K 36/185* (2006.01)

(52) U.S. Cl.
CPC ........... *A61K 36/185* (2013.01); *A61K 2236/39* (2013.01)

(58) Field of Classification Search
CPC ..................................................... A61K 36/185
See application file for complete search history.

(56) References Cited

U.S. PATENT DOCUMENTS

| | | | |
|---|---|---|---|
| 4,004,976 A | 1/1977 | Isaac | |
| 5,595,743 A | 1/1997 | Wu | |
| 5,997,888 A | 12/1999 | Weder et al. | |
| 6,024,960 A | 2/2000 | Kharazmi et al. | |
| 6,485,752 B1 | 11/2002 | Rein | |
| 6,800,433 B1 | 10/2004 | Honda et al. | |
| 2004/0224906 A1* | 11/2004 | Hoving et al. | 514/27 |
| 2006/0177525 A1* | 8/2006 | Takagaki et al. | 424/725 |
| 2007/0154575 A1 | 7/2007 | Shimoda et al. | |
| 2009/0061027 A1* | 3/2009 | Pandalis | 424/725 |
| 2010/0119630 A1 | 5/2010 | Feistel et al. | |
| 2011/0135721 A1 | 6/2011 | Walbroel et al. | |
| 2011/0300244 A1 | 12/2011 | Pischel et al. | |

FOREIGN PATENT DOCUMENTS

| | | |
|---|---|---|
| CN | 1928098 | 3/2007 |
| DE | 202006004872 U1 | 7/2006 |
| EP | 1071439 B1 | 1/2001 |
| EP | 1 837 029 A1 | 9/2007 |
| FR | 2897238 A1 | 8/2007 |
| JP | 06336421 | 12/1994 |
| JP | 2001072583 | 3/2001 |
| JP | 2001278792 | 10/2001 |
| JP | 2004113141 A | 4/2004 |
| JP | 2007261987 | 10/2007 |
| RU | 2240131 C1 | 11/2004 |
| RU | 2355240 C1 | 5/2009 |
| WO | 9215314 A1 | 9/1992 |
| WO | 9953934 A1 | 10/1999 |
| WO | 0064883 | 11/2000 |
| WO | 03043613 A2 | 5/2003 |
| WO | WO 2007031297 A2 * | 3/2007 |
| WO | 2007/110133 A1 | 10/2007 |
| WO | 2008003314 A1 | 1/2008 |
| WO | 2008006589 A2 | 1/2008 |

OTHER PUBLICATIONS

Demetzos et al. (1990) Journal of Natural Products vol. 53, No. 5 pp. 1365-1368.*
Guvenc et al. (2005) Pharmaceutical Biology vol. 43, No. 2, pp. 178-183.*
Demetzos et al. (1990) J. Natural Prods. vol. 53, No. 5 pp. 1365-1368.*
Droebner et al. (2007) Antiviral Res. 76: 1-10.*
Kroyer et al., "Evaluation of bioactive properties of pollen extracts as functional dietary food supplement," Innovative Food Science & Emerging Technologies 2(3):171-174 (Sep. 2001).
Blank, "*Cistus Incanus* Extract Relives Sore Throat", Deutsche Apotheker Zeitung, Deutscher Apotheker Verlag, Stuttgart, DE, 145(46):40-41 (Nov. 17, 2005).
Demetzos et al., "Hétérosides polyphénoliques des feuilles de *Cistus creticus* L", Ann. pharmaceutiques frangaises, 47(5):314-318 (1989).
Droebner et al., "CYSTUS052, a polyphenol-rich plant extract, exerts anti-influenza virus activity in mice", Antiviral Research, 76:1-10 (2007).
Ehrhardt et al., "A polyphenol rich plant ext4ract, CYSTUS052, exerts anti influenza virus activity in cell culture without toxic side effects or the tendency to induce viral resistance", Antiviral Research, 76:38-47 (2007).
Hoc, "Extract from *Cistus in canus* against influenza pandemic?", Zeitschrift Fuer Phytotherapie, Hippokrates Verlag in MVS Medizinverlage, DE, 28(3):142-143 (Jan. 1, 2007).

(Continued)

*Primary Examiner* — Chris R Tate
*Assistant Examiner* — Russell Fiebig
(74) *Attorney, Agent, or Firm* — Dardi & Herbert, PLLC; Peter S. Dardi

(57) ABSTRACT

The invention relates to a method for producing an extract containing at least 40% (m/m) of polyphenols from *Cistus creticus* L., said method comprising the following steps: plant parts are extracted from *Cistus creticus* L. using an extraction agent selected from the group comprising water, alcohols and mixtures thereof; the extraction residues are removed; the extraction agent is at least partially removed; redissolution is carried out in an aqueous solvent and the undissolved constituents are removed; and selective enriching is carried out by means of either a) a two-phase extraction, and b) a membrane filtration.

17 Claims, 1 Drawing Sheet

(56) References Cited

OTHER PUBLICATIONS

Kupeli et al., "Flavonoids with anti-inflammatory and antinociceptice activity from *Cistus laurifolius* L. leaves through bioassay-guided procedures", Journal of Ethnopharmacology, 112:524-530 (2007).
Richter, "Rock Rose (*Cistus*) cortra dysentery. Ancient knowledge revisited", MMW Fortschritt der Medizin, Urban und Vogel Medien und Medizin Verlagsgesellschaft, DE, 142(47):47-48 (Nov. 123, 2000).
Saracini et al., "Simultaneous LC-DAD and LC-MS Determination of Ellagitannins, Falvonoid Glycosides, and Acyl-Glycosyl Flavonoids in *Cistus salvifolius* L. Leaves", Chromatographia, 62(No. 5/6):245-249 (2005).
Wetherall et al., "Evaluation of Neuraminidase Enzyme Assays Using Different Substrates to Measure Susceptibility of Influenza Virus Clinical Isolates to Neuraminidase Inhibitors: Report of the Neuaminidase Inhibitor Susceptibility Network", Journal of Clinical Microbiology, 41(2):742-750 (Feb. 2003).
Yamaguchi et al- "Anabolic Effects of Bee Pollen *Cistus ladaniferus* Extract in Osteoblastic MC3T3-E1 Cells in Vitro", Journal of Health Science, 53(5):625-629 (2007).
Alter, "Use of the enzyme pectinase in the preparation of cholosa,s," Aptechnoe Delo, 6(3):50-52 (1957) Abstract Only.
Ameye et al., "Osteoarthritis and nutrition. From nutraceuticals to functional foods: a systematic review of the scientific evidence," Arthritis research & Therapy, 8:R127 (2006).
Brief et al., "Use of Glucosamine and Chondroitin Sulfate in the Management of Osteoarthritis," J. Am Acad Orthop Surg, 9:71-78 (2009).
Callard, "I feel it in my fingers . . . ", Natural Products (online article), Jul. 20, 2007, XP-002543525 (9 pages).
Cheryan, Ultrafiltration and Microfiltration Handbook, CRC Press, 1998, pp. 5-6.
Chrubasik et al., "A systematic review on the *Rosa canina* effect and efficacy profiles," Phytotherapy Research: PTR, 22(6):725-733 (2008).
Chrubasik et al., "The evidence for clinical efficacy of rose hip and seed: a systematic review," Phytotherapy Research: PTR, 20(1):1-3 (2006).
Conner et al., "Inflammation, Free Radicals, and Antioxidants," Nutrition, 12(4):374-3T7 (1996).
Deliorman Orhan et al., "In vivo anti-inplamniatory and antinociceptice activity of the crude extract and fractions from *Rosa canina* L. fruits," J. of Ethnopharmacology, 112(2):394-400 (2007).
Energy Group S.A., "Product Documentation—Skeletin," retrieved Apr. 17, 2013, www.energy.sk/files/2_vyrobky/PD_skeletin_EN_web.pdf.
Energy Group S.A., "Skeletin," http://web.archive.org/web/20070622074115/ http://www.energy.sk/info/vyrobky/skeletin.asp, Jun. 22, 2007, retrieved Mar. 24, 2014.
Gao et al., "Evaluation of antioxidant activities of rosehip ethanol extracts in different test systems," J. Sci Food Agric, 80(14):2021-2027 (2000).
Google Search Results provided by the European Patent Office for the expression "Artrevit" within the time period of Jan. 1, 2000 through Dec. 12, 2007.
Google Search Results provided by the European Patent Office for the expression "Skeletin" within the time period of Jan. 1, 2000 through Dec. 12, 2007.
Hakansson et al., "Rose Hip and *Lactobacillus plantarum* DSM 9843 Reduce Ischemia/Reperfusion Injury in the Mouse Colon," Dig Dis Sci 51:2094-2101 (2006).
Joachimova et al., "Skeletin se letos urcite hodi, ocekáváme ohen v kostech," Energy Magazin, Apr. 2006, http://www.energy.sk/cz/info/0604/0604.asp#6.
Kharazmi et al., "Rose hip inhibits chemotaxis and chemiluminescence of human peripheral blood neutrophils in vitro and reduces certain inflammatory parameters in vivo," Inflammopharmacology, 7(4):377-386 (1999).
Lee et al., "Purification and Concentration of Betalaines by Ultra Filtration and Reverse Osmosis", Journal of Food Science, 47(2):465-471, 475 (1982).
Munoz et al., "Effects of enzymatic treatment on anthocyanic pigments from grapes skin from chilean wine," Food Chemistry, 87(4):487-490 (2004).
Novotelnov et al., "Enzymic preparation of vitamin C concentrate enriched with vitamin P," Biokhimiya (Moscow), 14:398-404 (1 page) Abstract (1949).
Oesser et al., "Stimulation of type II collagen biosynthesis and secretion in bovine chondrocytes cultured with degraded collagen," Cell Tissue Res, 311:393-399 (2003).
Oesser et al., "Einfluss von Kollagenfragmenten auf Neusynthese and Degradation der extrazelluläaren Knorpelmathx," Orthopädische Praxis, 41(10):565-568. (See English language summary) (2005).
Oszmianski et al., "Possible use of enzymatic preparations in the production of cloudy juices of high vitamin content from fruits of the rose *Rosa rugosa*; rosehip pectin degradation and juice preparation with high ascorbic a cid content," Chemical Abstracts Service, Columbus, OH (1993) (1 page) Abstract.
Product Information for GorVita Artrevit, http://gorvita.com.pl, Szczawa, Malopolskie, Poland.
Product Documentation for Skeletin, produced by Energy Group, a.s., Prague, Czech Republic.
Rein et al., "A herbal remedy, Hyben Vital (stand. powder of a subspecies of *Rosa canina* fruits), reduces pain and improves general wellbeing in patients with osteoarthritis—a double-blind, placebo-controlled, randomised trial," Phytomedicine 11:383-391 (2004).
Salminen et al., "Characterisation of proanthocyanidin aglycones and glycosides from rose hips by high-performance liquid chromatography-mass spectrometry, and their rapid quanitification together with Vitamin C," Journal of Chromatography A, 1077:170-180 (2005).
Shmeleva et al., "Effect of vitamins C+P complex on lactic acid *streptococci* and the activity of its bacteriphage," 24(7):16-19 (1963) (1 page) Abstract.
Unknown, "Joint and Bone Combo," necombo.wordpress.com, Nov. 10, 2007 (4 pages).
Unknown, "Joint Flex 1000 with Chondroitin & Rosehip," vita.com/products.aura/HEPE10452.asp, 2000, author unknown (2 pages).

* cited by examiner

CISTUS EXTRACT CONTAINING ENRICHED SECONDARY PLANT INGREDIENTS

CROSS REFERENCE TO RELATED APPLICATIONS

This application is a national stage filing of PCT Application No. PCT/EP2009/055487 filed May 6, 2009, which claims priority to European Patent Application No. 08155699.5 filed May 6, 2008, each of which is hereby incorporated herein by reference.

FIELD OF THE INVENTION

The present invention refers to enriched extracts from *Cistus*, compounded formulations thereof, processes concerning their manufacturing, and their usage.

BACKGROUND OF THE INVENTION

Within the family of Cistaceae, *Cistus* forms a genus of 18 to 20 species. The evergreen subgenus *Cistus creticus* L. ssp. *eriocephalus* reaches a height of up to 1 m and smells aromatic. Its egg-shaped lanceolate leaves show an alternate pattern, while its flowers have five petals and a radial symmetry, which is characteristic for the whole family. The light pink, pink, or light purple colors are typical for the subtype. Preferred habitat is the eastern Mediterranean region.

Folk medicinal usages have been versatile and ranged from being used as adjuvant for topical, allergy-related itching, as well as for preventing and managing wounds caused by bacterial infections and mycosis. Traditionally, aqueous decoctions from the aerial plant parts from spring have been used for this. Similarly have recent publications reported about the successful usage of *Cistus* solutions for the treatment of neurodermititis (AD), acne vulgaris, as well as for treating inflammatory diseases of the mouth and throat. *Cistus* is also well-known for its usage as tea (e.g. Cystus® Bio Teekraut). Recommended dose here is 2.5 g of *Cistus incanus* for 1 liter of hot water. According to our analysis, up to 1 g of dissolved extractives with ca. 16% polyphenols can thus be ingested. Other providers of *Cistus*, who give no detailed information on the species, obtain their raw material from wild collectings, which in consequence lead to unsteady results in both, extractives (0.7-1.5 g), as well as polyphenol contents (11-21%). Such, not-standardized mixtures represent the natural polymorphism of the plant and offer no basis for the manufacturing of a standardized plant extract.

A detailed specification of the varieties and/or subspecies has only recently become urgently necessary and relevant because of a legal distinction in the plant varieties' rights (PVR) between *Cistus incanus* L. ssp. Pandalis®, or the brand name Cystus®, and *Cistus creticus* L. ssp. *eriocephalus* (also known as *Cistus incanus* L. ssp. *tauricus*). It is very difficult to distinguish between the different types, especially for persons lacking expert knowledge.

SUMMARY OF THE INVENTION

The oldest known preparations of *Cistus* deal with labdanum, a resin, which was mostly gained from the leaves and stems of *Cistus ladaniferus* L., *Cistus monspliensis* L., and *Cistus incanus* L. Because of its pleasant aroma, it was often incensed. Other utilizations included that of an expectorant to treat catarrhs of the respiratory tract, as well as plastri and unguenta (medical dressings) for wound management purposes.

Phytochemical analyses of genus *Cistus* have therefore traditionally concentrated on analyzing its lipophilic substances, especially of its essential oils and resins. Here, we find the normal structures of the terpene metabolism, such as mono-, sesqui-, and diterpenes, as well as alcohols and esters. Other analyses have focused on the polyphenol fractions of its flavonoids and tanning agents. Kaempferol, quercetin and apigenin proved to be the most basic parts of the structures. Samples of *Cistus creticus* ssp have proven to be outstandingly rich in polyphenols. Surprisingly, our analyses have revealed that the polyphenol fingerprint of *Cistus creticus* ssp. *eriocephalus* resembles another, well-known pattern: Similar to extracts of green tea, in the area of the important oligomer fractions, derivates of catechin, such as gallocatechin or even epigallocatechingallat (EGCG) can be found. The total content of polyphenols in the plant is generally rated at 4%, while the concentration in the leaves is substantially higher.

Polyphenols are widely known for their antioxidant behavior, which refers to their potential to combat free radicals. In the human body, these are especially "reactive oxygen species", which are often caused by environmental influences (UV-rays, chemical noxes), but also by an unbalanced, unhealthy diet. According to latest state-of-the-art knowledge, many diseases can be linked to "reactive oxygen species". Cell damages attributed to radicals can lead to a number of diseases (e.g. immune diseases, mental exhaustion, arthritis) if they are not limited by "antioxidant scavengers". Thus, measuring the antioxidant capacity oftentimes delivers decisive values. High contents in polyphenols simultaneously indicate a high antioxidant potential.

Current research on an extract of the pink rock rose (CYSTUS® 052; manufactured from *Cistus incanus* PANDALIS, 26% of polyphenols, less than 2% of monomers (gallic acid, epigallocatechin, catechin and epicatechin)) shows its ability to significantly inhibit the increase of influenza viruses in in-vitro experiments, without producing any occurrence of resistance (Ehrhardt C. et al., Antiviral Res., 76, 38-47, 2007). Likewise, these results could be verified in an in-vivo (mouse model) experiment (Droebner, K. et al., Antiviral Res. 76, 1-10, 2007).

Commercial products such as *Cistus incanus* capsules (Co. LR Health and Beauty Systems) generated from simple aqueous extracts (20-25% polyphenols; drug-extract-ratio of 2-4:1), represent the current technical state-of-the-art. Own analyses have confirmed that aqueous extractions from *Cistus incanus* ssp. *tauricus* or *Cistus creticus* L. ssp. *eriocephalus* can produce extracts with 20-28% polyphenol contents, depending on the quality of the used raw materials.

In order to be able to evaluate and compare different formulations of *Cistus*, a clear definition of the species is necessary. Furthermore are both, specifications concerning the manufacturing (extractant; drug-to-extract ratio), as well as an analytical characterization (polyphenols), necessary requirements for a standardized product. Only a reproducible, standardized extract quality will ensure a stable therapeutic scheme for therapeutical usages. The invention was aimed at providing a method for manufacturing a *Cistus* extract with a high content, which will—in a reproducible way—produce standardized extracts of preferably a minimum content of 40% (w/w) polyphenols.

This task is accomplished by a method of manufacturing an extract from *Cistus* using the following steps:
Extracting of plant parts of *Cistus* L. with solvents selected from the group of water, alcohols and mixtures thereof
removal of extraction residues
at least partial removal of extractants Redissolving into an aqueous solvent and removal of indissoluble compounds
selective enrichment by means of at least one of the following steps:
a) a two-phase extraction
b) a membrane filtration Preferable for such a manufacturing procedure will be a constant quality of plant raw material. This can be achieved by analyzing its contents in polyphenols (stated with the help of Folin's reagent and calculated as gallus acid according to Method of European Pharmacopoeia, chapter PH. EUR. (2.8.14)), and afterwards by mixing different batches.

In order to obtain a higher proportion of leaf material over stalk fractions, the drug is ground as well as air-swept. The leaves have a higher content of polyphenols. Thus, an improvement of 30% can be reached. *Cistus creticus* L. ssp. *eriocephalus* is preferred. Preferably, aerial plant parts are used.

Generally, raw materials with a content of a minimum of 12% polyphenols are preferred.

Water, methanol, ethanol, 1-propanol, 2-propanol, and mixtures thereof have proven suitable as extractants. Preferably, the content of alcohol does not exceed 50% (v/v), preferably not more than 40% (v/v), or not more than 30% (v/v).

One possible embodiment of extraction uses an elevated level of temperature. Temperatures ranging from 40° to 80° C. are especially preferred in order to gain a high yield of polyphenols.

After extraction, drug residues are removed, which can be done either by filtration or by suction and later squeezing of the drug residue. Further possible methods are known by experts.

Afterwards, the extractant is at least partially removed from the obtained extract. This can be achieved by a rotary evaporator which removes the solvent, or with the help of a panel evaporator. A gentle treatment is preferred.

After removal, the ratio of the dry substance is preferably more than 50% (w/w).

In a next step, the remaining residues are redissolved. Here, especially water or mixtures from water and alcohol are suitable. Preferably, the redissolver consists of a minimum of 50% of water.

After redissolving, the remaining residue can be removed by methods such as filtration, suction, decanting, or the likes, and then be disposed. The remains will contain at least a part of the tannins (little bioactive polyphenols).

Afterwards, a step of enrichment follows. Either a two-phase extraction or a membrane filtration can be used.

The two-phase extraction can be a liquid-liquid extraction. n-Butanol has proven especially useful as an extractant for this liquid-liquid extraction.

Alternatively, or in addition to that, it is possible to conduct a solid-phase extraction. An extraction using adsorption resins is especially useful for this. Typical adsorption resins are for example non-ionic hydrophobic divinylbenzen-copolymers, aliphatic ester polymers and formophenol polymers. Such adsorbers are commercially traded by the name of Amberlite®. Adequate products are types XAD2, XAD4, XAD7HP, XAD16, XAD761, or XAD1180. Also resins produced by other manufacturers such as Diaion (SP-series), or Bayer (Lewatite®), or Miontech (P-series), can be used, as long as they are characterized as being analogous.

Resin type Amberlite® XAD7HP is especially preferred.

Alternatively, a membrane filtration can be conducted. Pore-defined materials made from polyestersulfon, polypropylene, polytetrafluoroethylene, or cellulose acetate are especially useful as membranes. Appropriate pore-sizes range from 70-100 kDa. The membranes can be installed in several layers into filter panels. Thus, ca. 60% of the polyphenols remain in the retentate (enriched product phase). Membranes made of polyestersulfon are especially preferred.

During a liquid-liquid extraction, the polyphenol-containing, aqueous phase is treated with an organic solvent such as n-butanol. In the course of intense mixing, the polyphenol substances transfer into the organic phase, which is then further treated.

When conducting a solid-phase extraction, the polyphenols selectively remain on the solid phase, before they can be diluted and separated as a liquid phase via an elution change to a more lipophilic solvent, such as ethanol. The organic phase is then further processed.

A membrane filtration separates polyphenols according to their size by pores. Secondary metabolites are held back by pores by means of their size. Together with the filtrate, other attendant substances such as salts and simple acids are separated. An enriched polyphenol fraction remains in the retentate.

Afterwards the solvent is removed from the extract by means of a vacuum, which is then dried in order to gain a dry extract. Drying should proceed as gently as possible.

Body of invention is also the extract obtained by the aforementioned procedure.

In its preferred embodiment, the extract is characterized by at least one of the following features:
a native drug-to-extract ratio (DEV native) of 4-40:1
an ORAC value of bigger than 3000 μmol trolox equivalent/g
a total polyphenol content of more than 40%, preferably >60% (w/w) and/or
a content of monomers of at least 2% (w/w)

Surprisingly, it was found that the invented *Cistus* extract exerts its effect via an inhibition of NF-κB.

NF-κB is an important specific transcription factor, has many target genes, and exerts many different effects. The activation of NF-κB is held for playing a critical role in the development of inflammations. Because of its many functions, NF-κB is linked to a large number of diseases. It is often unclear in how far the activation of NF-κB actually causally affects the progression of a disease. Since such a role is more and more seen as probable, the parts of NF-κB signaling pathways have in the meantime become important target structures for the development of new drugs. NF-κB can be attached to a specific DNA-motif, the so-called κB-motif, which consists of about ten base pairs. In the vast majority of cases, attaching NF-κB to the DNA-motif will lead to an increased transcription of the depending genes. At the moment it is thought that about 200 different genes are regulated by NF-κB. Among these are many cytokines (e.g. TNF-κ, and IL-1β), as well as adhesion molecules, which play an important role in regulating the immune system, especially with regard to inflammatory reactions.

Amongst others viral anti genes (e.g. lipopolysaccarides) belong to the stimuli which are able to trigger an activation of NF-κB.

Allergic inflammatory reactions are also set off via this NF-κB signal cascade, and can thus be reduced with an inhibiting influence.

So-called A549 lung cells were used as test models. The effects of the invented *Cistus* extract on the transcriptional activity of NF-κB were examined. The cell system was connected to a luciferase measuring system. After having measured the blank values, the synthetic substance PMA was added as stimulus which enhances the luciferase gene expression in A549 cells significantly. *Cistus* extracts in varied doses were introduced into the system. A clear dose-dependent inhibition could be shown.

|  | Concentration of *Cistus* extract [µg/ml] | | | | |
| --- | --- | --- | --- | --- | --- |
|  | 1 | 10 | 50 | 100 | 150 |
| Inhibition of NF-κB [%] | none | none | 22 | 42 | 65 |

Since A549 cells possess binding sites for two possible transcription factors —either for NF-κB or for AP-1—also the AP-1 binding site was examined with regard to its specifity. After having added a AP-1 luc plasmid to measure the activity of luciferase, the following results were obtained:

|  | Concentration of *Cistus* extract [µg/ml] | | | | |
| --- | --- | --- | --- | --- | --- |
|  | 1 | 10 | 50 | 100 | 150 |
| Inhibition of AP-1 [%] | none | none | +52 | +50 | +92 (activation) |

An activation of the AP-1 transcription factor could be stated. The results prove that it is a specific NF-κB induced inhibition, and that errors in measuring can be ruled out. The negative cytotoxicity test also demonstrated the proven results.

In order to verify the newly discovered mode of action via NF-κB, another model was chosen, where NF-κB itself has an effect on TNF-alpha (tumor necrosis factor-alpha), which in turn is known from anti-inflammatory research. Afterwards it could be tested whether *Cistus* extract influences a NF-κB induced activation of TNF-alpha (canonic pathway). A cloned cell line 5.1 was used, in which there was one luciferase gene from promoter HIV-1-LTR. The cells were pre-incubated with increasing extract doses, and stimulated with TNF cells for 6 hours. Afterwards, the cells were separated and the report activity in the luciferase model was measured. A dose-related inhibition of the HIV-1-LTR-gene transcription, which depends on TNF-alpha, could be shown (see FIG. 1). Here, the invented extract, with >40% polyphenols, turned out to be significantly more potent than an aqueous extract with >20% polyphenols, which represents the current technical state-of-the-art.

The influence of the invented extract on the NF-kappaB signaling pathway was verifiably confirmed.

The method produces an extract better suitable than former extracts for the following usages:
  Treatment or prophylaxis of viral diseases
  Treatment or prophylaxis of allergy-related inflammatory reactions, especially of allergic rhinitis
  Treatment or prophylaxis of disease patterns that accompany a common cold, such as rhinitis, sinusitis, laryngitis, chorditis
  Treatment of postviral fatigue syndrome
  Treatment of influenza, cholera, clostridic myositis, enteritis necroticans, herpes infections.

Subject of the present invention is also an extract formulation containing the invented extract.

Subject of the present invention is also a pharmaceutical formulation or a food/dietary supplement, containing the invented extract OR the invented extract formulation.

The first contact between a virus and a potential host usually takes place on the mucosa. Accordingly, a local application of the extract onto the mucosa leads to good results. In addition to common treatments in the mouth and throat as a lozenge or as a mouthwash against tonsillitis or gingivitis, treatment surprisingly also showed to be effective against disease patterns that frequently accompany a cold, such as inflammations of the nasal mucosa, the sinuses, the larynxes, and the vocal chords.

Surprisingly, it was also found that the invented *Cistus* extract has a high inhibitory effect on neuraminidase activity.

Neuraminidases are a family of enzymes of influenza viruses (type A and B) and other viruses that cut terminal sialic acidic rests from glycoproteins on cell surfaces of virus host cells, or viruses themselves. This procedure promotes the detachment of daughter viruses from infected cells. So-called neuraminidase-inhibitors are drugs that decrease the procedure of detaching from the host cell after a viral infection, and thus reduce the (systemic) free viral load. It is generally assumed to be important to take the drug immediately after the first symptoms, since the body's own immune defense at this point is not exhausted yet, but can be boosted by a medicinal reduction of the virus load. Both, Tamiflu® (Oseltamivir) and Relenza® (Zanamivir), which are hoped to help control a potential pandemic of bird flu (virus H5N1), belong to this type of drugs. Unfortunately, such chemical neuraminidase-inhibitors often cause side effects such as nausea, stomach pain, and vomiting. Furthermore have first resistances against these drugs been observed.

Since plant extracts possess a well-known benefit-to-risk profile even over longer periods of intake, the invented *Cistus* extract was tested in comparison to Zanamivir in an in-vitro enzyme model (NA-Star®) according to Wetherall N T, Trivedi T, Zeller J, Hodges-Savola C, McKimm-Breschkin J L, Zambon M, Hayden F G. Evaluation of neuraminidase enzyme assays using different substrates to measure susceptibility of influenza virus clinical isolates to neuraminidase inhibitors: report of the neuraminidase inhibitor susceptibility network. Clin Microbiol. 2003 Feb; 41 (2): 742-50.

In order to show the effectiveness of the invented extract, the neuraminidases of the following species were tested:

| Virus Species | IC 50 [mg/mL] *Cistus* Extract 60% Polyphenols | IC 50 [µM] Zanamivir |
| --- | --- | --- |
| *Clostridium perfringens* | 36.2 | >>200 |
| *Vibrio cholerae* | 43.1 | 200 |
| Influenza A H1N1 | 36.7 | <<0.01 |

For the invented extract, a remarkable neuraminidase inhibition could be demonstrated, independently from the tested virus species. Thus, the following application areas arise: influenza, cholera, clostridium-myotis, enteritis necroticans.

In addition, a quite universal usability of the invented extract on viral diseases could be shown with herpes simplex viruses type 1 (HSV-1):

In order to define the virucidal activity, a viral suspension is exposed to the extract and then the infectiousness of viruses in the cells is measured. Ethanol is used for positive controls.

The definition of virustatic activity is then identified via the supernatant of infected human cells after inoculation with extract. Aciclovir is the accepted positive control.

| Virus Species Herpes Simplex Virus I | IC 50 [µg/mL] *Cistus* extract 60% Polyphenols | IC 50 [µg/mL] Aciclovir | IC 50 [µg/mL] Ethanol |
| --- | --- | --- | --- |
| Virucidal | 3.5 | ineffective | 80,000 |
| Virustatic | 10.3 | 0.2 | ineffective |

For the invented *Cistus* extract with 60% of polyphenols both, a remarkable virucidal as well as virustatic activity could be demonstrated.

Surprisingly, in practical application even an effect on the postviral fatigue syndrome could be shown. The administration of *Cistus* drops (20 drops three times a day), manufactured according to example 10, showed a significantly faster recovery after the diagnostic finding of an influenza infection within 2-3 days than without medication (4-7 days) in three male test persons aged 40-42 years old.

There are many names for the postviral fatigue syndrome, such as royal-free disease, myalgic encephalomyelitis, epidemic neuromyastheny, chronic mononucleosis, chronic Epstein-Barr virus, chronic exhaustion syndrome, or, to keep it short, postviral syndrome. Current research suggests that the disease could be caused by special viruses, such as the Epstein Barr-virus, also initiator of infectious mononucleosis. The symptoms oftentimes only show after an acute infection (often with fever, shivering, bodily pain, enlarged lymph glands, and exhaustion) has already decreased. After the disease has seemingly ended, the patient begins to feel uneasy once again and different ailments will from then on persistently remain. Main symptoms are profound weakness, pain of the muscles, problems with memory and concentration, exhaustion and a persisting or frequent flu-like feeling.

Further distinguishing between the numerous types of postviral fatigue syndromes is not too relevant at this point. The disease is diagnosed and treated according to normal principles. Treatment can possibly take several months with slow progressions of the disease, though in many cases an autonomous improvement of the symptoms can be seen.

Further application areas are influenza (also H5N1 and H1N1), and herpes simplex infections.

The invented *Cistus* extract formulations have inhibiting influence on the NF-κB signaling transduction and can thus be used against (local) allergic infectious reactions in the mouth or throat. Because of its extra activity as neuraminidase inhibitor, appropriate extract formulations can also be used for the treatment and prophylaxis of rhinitis and sinusitis, as well as against postviral fatigue syndromes.

Tinctures, syrups, brushings, mouthwashes, (nasal) drops, nasal sprays, powder inhalations, or inhalation solvents are all suitable forms for applying the invented extract. At the same time, dried forms of the invented extract are obtainable for intake as capsules, tablets, dragées, pastilles, soft tablets or lozenges, but also redissolved as a powder, granulate or as an effervescent formulation. In order to have a high concentration locally quickly available, a melting tablet or lyophilizate is especially useful.

DETAILED DESCRIPTION OF THE INVENTION

Figure 1:
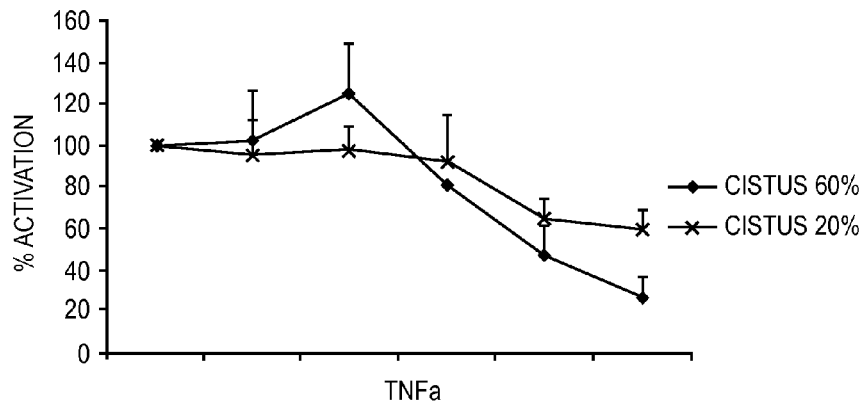
FIG. 1 shows effects of *Cistus* extracts on TNF-alpha induced NF-kappaB transcription.

The underlying HPLC-requirements are as followed:
Binary high pressure gradient system, i.e. consisting of:

| | |
|---|---|
| 2 pumps: | Model 510 or 515 (Co. Waters) |
| Injector: | Autosampler W 717 (Co. Waters) |
| Column: | Steel column 250 × 4.6 mm Luna Phenyl-Hexyl, 5 μm (Co. Phenomenex) |

-continued

| | |
|---|---|
| Column oven: | Jetstream Plus (Co. VDS Optilab) |
| Detector: | Tunable Absorbance detector W 2487 (Co. Waters) |
| Integrator: | HPLC evaluation software |
| Fluxing agent: | A: 180 ml acetonitrile, 40 ml acetic acid and 4.0 ml of EDTA-solvent are filled into a 2000-ml-volumetric flask and filled up with water R almost completely. After raising the temperature to room temperature, water R is added up to the calibrations mark.<br>B: 800 ml acetonitrile, 20 ml acetic acid and 2.0 ml EDTA-solvent are filled into a 1000 ml volumetric flask and filled up with water R almost completely. After raising the temperature to room temperature, water R is added up to the calibrations mark. |
| Flow: | 1.0 ml/min, gradient |
| Lingering volume: | 2.45 ml (mode routine 2) |

| Flow rate [ml/min] | Time [min] | Eluent A [%] | Eluent B [%] | |
|---|---|---|---|---|
| 1.0 | 0 | 100 | 0 | Separation |
| 1.0 | 10 | 100 | 0 | |
| 1.0 | 25 | 68 | 32 | |
| 1.0 | 35 | 68 | 32 | |
| 1.0 | 40 | 100 | 0 | Conditioning |
| 1.0 | 60 | 100 | 0 | |

| | |
|---|---|
| Column temperature: | 35° C. |
| Injection volume: | 10 μl |
| Detection: | Absorption in UV-light at 278 nm |

The invention will be illustrated further with the help of the following examples:

EXAMPLE 1

Evaluation of the *Cistus* Raw Material

Regrowing, aerial plant parts (leaves, flowers, stems) are used as raw material for the drug. They are dried gently, shredded to an extraction size of about 10 mm, and separated from their stalk fractions by air sweeping.

1000 g primary plant extract together with hot water (90°) are put into a percolator and extracted for five hours. After extraction time, it is filtered off, and the extraction is repeated. For the second run, the extraction time takes 3 hours. Afterwards, both extracts are combined and concentrated to a spissum in a rotary evaporator. Now the spissum extracts of each *Cistus* species is analyzed via the DPPH-method with regard to their antioxidant potential.

This method is based on a redox reaction with the stable radical 2.2 diphenyl-1-pikrylhydracyl (DPPH). Thus, the extract's ability to act as a direct antioxidant can be measured. The DPPH radical has a purple color, which is due to the unpaired electron at the nitrogen atom. As soon as the radical attaches itself to one hydrogen atom of a scavenger, the reduced DPPH-H (2.2 diphenyl-1-picrylhydrazin) develops. The antioxidant effect can then be measured by a photometrical measurement of the decrease of the absorption at 517 nm. An inhibition rate of 50% is given.

| Cistus species | IC 50 [µg/mL] |
|---|---|
| *Cistus ladanifer* L. | 7.9 ± 0.7 |
| *Cistus florentinus* | 3.1 ± 0.2 |
| *Cistus monspeliensis* L. | 2.8 ± 0.2 |
| *Cistus canescens* | 2.0 ± 0.2 |
| *Cistus creticus* L. ssp. *creticus* | 1.3 ± 0.2 |
| *Cistus creticus* L. ssp. *eriocephalus* | 1.0 ± 0.1 |

Result: aqueous extracts from the species *Cistus creticus* L. are superior to the other species when looking at their antioxidant potential. Especially potent are extracts of the subspecies *Cistus creticus* L. ssp. *eriocephalus*.

EXAMPLE 2

Aqueous Raw Extract

An aqueous extract is manufactured from 10 kg of the drug Herba *Cistus creticus* L. ssp. *eriocephalus* (polyphenol content of 12.3%), and 20 times as much water at 80° C. by exhaustive percolation. After a vacuum-concentration, the aqueous extract has a dry matter ratio of 60%. The yield of native extract amounts to 5 kg. The polyphenol content amounts to 20.0% calculated to the native extract.

EXAMPLE 3

Ethanolic-Aqueous Raw Extract 15.5 kg of the drug Herba *Cistus creticus* L. ssp. *eriocephalus* (polyphenol content of 14.6%) are exhaustively extracted two times in the percolator at 40° C. with ethanol 40% (v/v) at 1:8. After having separated the eluates from the drug, they are combined and filtered before being gently freed from the solvent at 50° C. in a vacuum. 6 kg aqueous spissum extract with a dry matter ratio of 65% (=3.9 kg native extract) result from this procedure. The polyphenol content amounts to 31.4% in relation to the native extract.

EXAMPLE 4

Extract Re-Solution 5.8 kg spissum (3.77 kg native extract) of the extract—as obtained according to example 3—are redissolved to 20% of dry matter and intensely homogenized for 60 minutes, by stirring. Afterwards, the preparation rests for 4 hours at 10-15° C. Insoluble sediment (5% of the total content) has settled on the ground. This sediment (tannin fraction) shows a polyphenol content of 22% in relation to the native extract.

The supernatant (product phase) is stripped from above and cleared through a CP1KS filter panel (yield: 95%). The polyphenol content was 32.0% in relation to the native extract.

EXAMPLE 5

Solid-Phase Extraction

Figure 2:
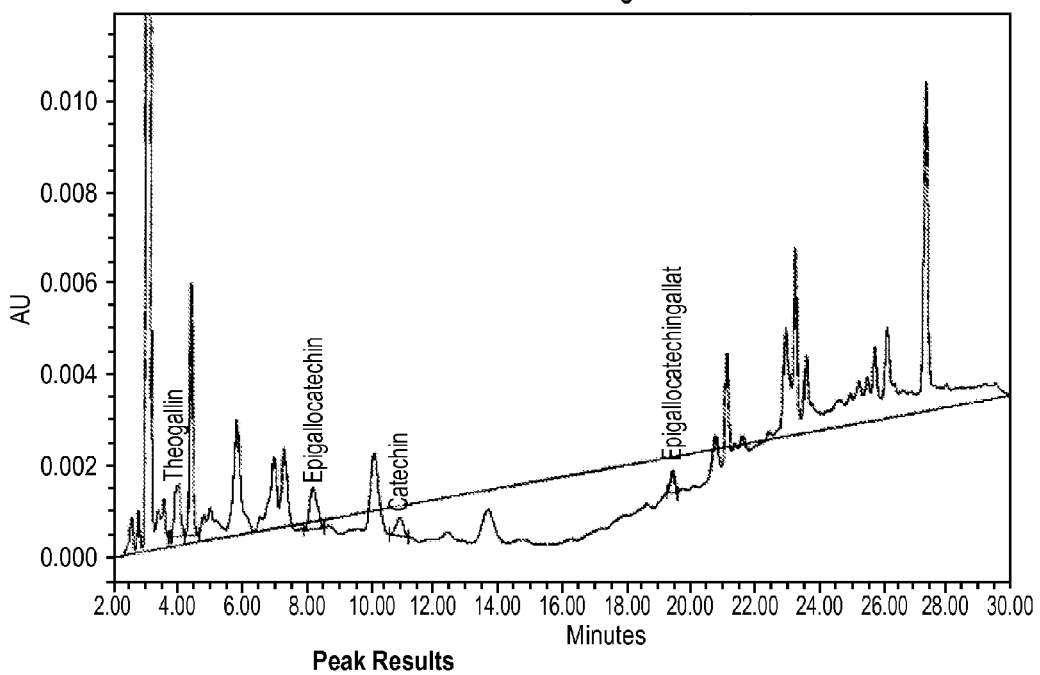
FIG. 2 shows an HPLC-fingerprint of the extract according to example 5.

The extract solution according to example 4, containing 3.58 kg of native extract as ca. 20% solution, is added to a column, which is filled with 50 L adsorber resin (Amberlite® XAD7HP). The first cycle is separated and then discarded. Then, the column is cleaned with 3 channel volumes (150 L) of water. The elution of the adsorbed secondary *Cistus* metabolites takes place with 100 L of ethanol 96% (v/v). The ethanol-water eluate is collected, filtered, removed from its solvent by vacuum, and then evaporated to a spissum. 2 kg of spissum with a dry matter of 65% (=1.3 kg native extract) result. The polyphenol content amounted to 65.0% in relation to the native extract. The ratio of monomers (theogallin, epigallocatechin, catechin, epicatechin, and also epigallocatechingallat) amounts to 3.6%. The extract is characterized by a specific HPLC fingerprint (see FIG. 2).

EXAMPLE 6

Dry Extract

Spissum extract—as obtained according to example 5—is spray-dried. For this, the spissum is adjusted to a dry matter of 40% with water and loaded to the spray dryer, which has an airstream temperature of 180° C. A fine powder results after the atomization in the tower, which leaves the tower in an airstream at 100° C. However, the product temperature of the extract does not exceed 55° C. A fine powder (95% <0.315 mm) results, with a loss on drying of 4%. The polyphenol content was 64.8% in relation to the native extract.

EXAMPLE 7

Membrane Filtration 100 g of spissum extract—as obtained according to example 3—(65 g native extract ratio) are redissolved with demineralized water to 5% dry matter and cleared from sediments. Afterwards, the pH-value is set to 4.5-5.0.

During two hours, the solution is separated into two fractions via a tangential flow filtration using a 100 kDa membrane (polyethersulfone). A filtered permeate phase as well as a retained retentate phase constitutes.

Both phases are evaporated to a spissum in a vacuum.

| Phase | Retentate | Permeate |
|---|---|---|
| Amount in relation to dry matter | 45% | 55% |
| Polyphenol content in relation to native extract | 44.4% | 15.4% |

The enriching of polyphenols in the retentate proceeds specifically, while even producing a significantly higher content than could be assumed from the mass relationship. In comparison to the initial extract with 31.4% of polyphenols, the content could be increased by 42%.

EXAMPLE 8

Liquid-Liquid Extraction 100 g native extract—as obtained according to example 7 (retentate phase)—is set up to a 20% dry matter ratio with water. Afterwards, it is intensely mixed 3× with 1/3 volume parts n-butanol in a separating funnel at room temperature. After having rested for 30 minutes, a clear phase separation develops. The n-butanol phase is separated from the aqueous phase.

The combined organic phases, as also the water phase, were concentrated to a spissum while removing the solvents with the help of a rotary evaporator.

| Phase | Organic phase | Water phase |
| --- | --- | --- |
| Amount in relation to dry matter | 16% | 84% |
| Polyphenol in relation to native extract | 63.7% | 27.6% |

The enriching of polyphenols through the organic phase is specific and produces an increase of about 49% in comparison to the initial extract with 31.4% of polyphenols.

EXAMPLE 9

Antioxidant Potential

ORAC (oxygen radical absorption capacity) is an internationally standardized method in order to define antioxidant potentials. By means of this method, a distinction between hydrophilic and lipophilic parts of the antioxidant effect is possible. For better comparability, the total capacity is given in the unit of the trolox equivalent (TE). The actual procedure is described on www.orac-europe.com.

The invented Cistus extract (60% polyphenol)=5100 μmol TE/g

Aqueous Cistus extract (25% polyphenols)=1900 μmol TE/g

The invented enriched Cistus extract has an outstandingly high ORAC potential, which is higher than the current state-of-the-art by a factor of 2.7. Enriching polyphenolic compounds from Herba Cistus L. correlates with its antioxidant potential.

The concentration of oxygen radicals (superoxide anions) is regarded as measure for oxidative stress in organic tissues. By means of quantifying superoxide anions with a color reduction after stimulating with phorbol-12-myristat-13-acetate (PMA), the following antioxidative capacities have been recorded (test concentration 200 μg/ml) in comparison to an untreated control (0% inactivation):

The invented Cistus extract (60% polyphenols): 65.0±8.9%

Aqueous Cistus extract (25% polyphenols): 20.5±9.3%

Vitamin C (methodical standard): 96.6%±11.3%

The invented Cistus extract (60% polyphenols) has an outstandingly high antioxidant capacity for inactivating free oxygen radicals, which is increased by a factor of 3.2 in comparison to current state-of-the-art.

EXAMPLE 10

Drop Formulation

Purified ethanolic extract—as obtained according to example 5—is redissolved into water to a dry matter of 12%. Afterwards, 20% glycerol is added while stirring. Thus, a drop formulation was obtained, which has an improved taste, and a longer endurance.

EXAMPLE 11

Application as Nasal Drop

A drop formulation manufactured according to the aforementioned example 10 was used by a male proband, aged 38, in the course of a violent hay fever sneezing attack. He used it nasally in the form of drops from a pipette. After only a few minutes, his nasal mucosa was no longer swollen and reduced to its normal size.

EXAMPLE 12

Usage as Nasal Spray

A drop formulation manufactured according to the aforementioned example 10 was used by a male proband, aged 56, in the course of a violent hay fever sneezing attack. He used it nasally, nebulized to a mist from a nasal spray. By the spray dose, the sneezing attack was reduced after a few minutes.

The invention claimed is:

1. An enriched extract comprising at least 40% (w/w) polyphenols from *Cistus creticus* L., obtained by a process comprising the steps of:
   a. mixing aerial plant parts of *Cistus creticus* L. with an extractant solvent selected from the group consisting of water, methanol, ethanol, 1-propanol, 2-propanol and mixtures thereof, to produce an extraction mixture;
   b. removing extraction residues and at least partially removing the extractant solvent from the extraction mixture to produce a crude extract;
   c. redissolving the crude extract in an aqueous solvent having at least 50% (w/w) water, and removing insoluble components to produce a refined extract;
   d. enriching the refined extract by at least one of the following steps:
      1. solid-phase extraction, wherein the polyphenols bind to the solid phase and are eluted by more lipophilic solvents,
      2. liquid-liquid extraction, where in the organic solvent phase is the product phase;
      3. membrane filtration, wherein the retentate is the product phase.

2. The extract according to claim 1 with a native drug-to-extract ratio (DERnative) of 4-40:1, an oxygen radical absorption capacity (ORAC) value of more than 3000 μmol of trolox equivalent per gram, a total polyphenol content of more than 40% (w/w), and a content of monomers of at least 2% (w/w).

3. An extract formulation containing an extract according to claim 1 and antioxidants.

4. A pharmaceutical formulation or food product containing an extract formulation according to claim 3.

5. The extract according to claim 1 with a total polyphenol content of more than 40% (w/w) relative to the total dry matter content.

6. A pharmaceutical formulation or food product comprising the extract according to claim 1.

7. The pharmaceutical formulation or food product of claim 6 having a form of a tincture, syrup, mouthwash, (nasal) drop, nasal spray, powder inhalation, or inhalation solvent.

8. The pharmaceutical formulation or food product of claim 6 having a form of a capsule, tablet, dragée, pastille, soft tablet or lozenge.

9. The pharmaceutical formulation or food product of claim 6 being a food product.

10. A process for preparing an extract comprising at least 40% (w/w) of polyphenols based on dry weight of the extract from *Cistus creticus* L., comprising the steps of:
   a. mixing aerial plant parts of *Cistus creticus* L. with an extractant solvent selected from the group consisting of water, methanol, ethanol, 1-propanol, 2-propanol and mixtures thereof, to produce an extraction mixture;
   b. removing extraction residues and at least partially removing the extractant solvent from the extraction mixture to produce a crude extract;

c. redissolving the crude extract in an aqueous solvent having at least 50% (w/w) water, and removing insoluble components to produce a refined extract;
d. enriching the refined extract by at least one of the following steps:
1. solid phase extraction, wherein the polyphenols bind to the solid phase and are eluted by more lipophilic solvents
2. liquid-liquid extraction, where in the organic solvent phase is the product phase;
3. a membrane filtration, wherein the retentate is the product phase.

11. The process according to claim 10, wherein said extractant solvent is selected from the group consisting of water, ethanol and mixtures thereof.

12. The process according to claim 10, wherein the mixing step is performed at a temperature of from 40 to 80° C.

13. The process according to claim 10, wherein said at least partially removing of the extractant solvent is performed to obtain a dry matter content of >50% (w/w).

14. The process according to claim 10, wherein the organic solvent in the liquid-liquid extraction, is n-butanol.

15. The process according to claim 10, wherein said solid-phase extraction is performed with an adsorber resin selected from the group consisting of non-ionic hydrophobic divinylbenzene copolymers, aliphatic ester polymers and formophenol polymers.

16. The process according to claim 10, wherein said plant parts are derived from *Cistus creticus* L. ssp *eriocephalus*.

17. The process according to claim 10, further comprising a step of drying the extract.

\* \* \* \* \*